US012626439B2

(12) United States Patent
Liu

(10) Patent No.: US 12,626,439 B2
(45) Date of Patent: May 12, 2026

(54) METHODS AND SYSTEMS FOR CORRECTING PROJECTION DATA

(71) Applicant: SHANGHAI UNITED IMAGING HEALTHCARE CO., LTD., Shanghai (CN)

(72) Inventor: Yanyan Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 363 days.

(21) Appl. No.: 18/344,816

(22) Filed: Jun. 29, 2023

(65) Prior Publication Data

US 2023/0342997 A1 Oct. 26, 2023

Related U.S. Application Data

(63) Continuation of application No. PCT/CN2022/071843, filed on Jan. 13, 2022.

(30) Foreign Application Priority Data

Jan. 13, 2021 (CN) .......................... 202110045078.5

(51) Int. Cl.
G06T 11/00 (2006.01)
A61B 6/00 (2024.01)

(52) U.S. Cl.
CPC ............ *G06T 11/006* (2013.01); *A61B 6/482* (2013.01); *A61B 6/5205* (2013.01); *G06T 2211/408* (2013.01)

(58) Field of Classification Search
CPC . G06T 11/006; G06T 2211/408; A61B 6/482; A61B 6/5205
(Continued)

(56) References Cited

U.S. PATENT DOCUMENTS 9,916,648 B1 3/2018 Tseng et al.
11,089,960 B2 * 8/2021 Shapira .................... A61B 6/48
(Continued)

FOREIGN PATENT DOCUMENTS

CN 102609908 A 7/2012
CN 105225208 A 1/2016
(Continued)

OTHER PUBLICATIONS

International Search Report in PCT/CN2022/071843 mailed on Apr. 15, 2022, 5 pages.
(Continued)

*Primary Examiner* — Allen H Nguyen
(74) *Attorney, Agent, or Firm* — METIS IP LLC

(57) ABSTRACT

The present disclosure provides a method and system for correction projection data. The method includes: obtaining the entity projection data and the transformed projection data related to the imaging object, the transformed projection data includes the first projection data related to the pixel shading generated by the detector components; inputting the entity projection data, the transformed projection data to the trained correction model and obtaining the correction projection data. The correction model obtained through training realizes the efficient and accurate correction of multi-energy imaging/spectral radiography, so that the obtained correction projection data may be more in line with the complexity of the actual system, and the correction effect may be better.

20 Claims, 5 Drawing Sheets

100

(58) Field of Classification Search
USPC .......................................................... 382/131
See application file for complete search history.

(56) References Cited

U.S. PATENT DOCUMENTS

| | | | |
|---|---|---|---|
| 2017/0325775 A1 | 11/2017 | Jiang et al. | |
| 2018/0192985 A1* | 7/2018 | Maass .................... | A61B 6/032 |
| 2019/0005686 A1 | 1/2019 | Liu | |
| 2021/0049810 A1* | 2/2021 | Dennerlein .............. | A61B 6/03 |
| 2022/0292736 A1* | 9/2022 | Chukalina ............. | G06T 11/005 |

FOREIGN PATENT DOCUMENTS

| | | | |
|---|---|---|---|
| CN | 106683143 A | 5/2017 | |
| CN | 107330949 A | 11/2017 | |
| CN | 108109185 A | 6/2018 | |
| CN | 108670282 A | 10/2018 | |
| CN | 111627083 A | 9/2020 | |
| WO | 2022152218 A1 | 7/2022 | |

OTHER PUBLICATIONS

Written Opinion in PCT/CN2022/071843 mailed on Apr. 15, 2022, 5 pages.
First Office Action in Chinese Application No. 202110045078.5 mailed on Jul. 25, 2022, 15 pages.

* cited by examiner

<u>100</u>

<u>300</u>

400

METHODS AND SYSTEMS FOR CORRECTING PROJECTION DATA

CROSS-REFERENCE TO RELATED APPLICATIONS

This application is a continuation of International Application No. PCT/CN2022/071843, filed on Jan. 13, 2022, which claims priority to Chinese Patent Application No. 202110045078.5, filed on Jan. 13, 2021, the contents of each of which are hereby incorporated by reference.

TECHNICAL FIELD

The present disclosure generally relates to systems and methods for image processing, and in particular, to systems and methods for correcting projection data.

BACKGROUND

Multi-energy imaging/spectral radiography exploits different absorption rates of radiation of different ray energies by tissue, organs, and/or materials to generate an image that may allow differentiation of such tissue, organs, and/or material compositions. In multi-energy imaging/spectral radiography, as the rays emitted are in a broadband spectrum, beam hardening may occur during the ray transmission process, resulting in different attenuation at different positions, and further appearing in the projection data, as well as in an image as an artifact (e.g., a cup-shaped artifact). In addition, one or more additional artifacts may occur caused by a deviation of an installation position of a component of an imaging device (e.g., a detector, or a portion thereof) used to acquire the projection data relative to a reference position (e.g., an ideal position), a ray obstructed by a component of the imaging device (e.g., detector, or a portion thereof), etc. Therefore, methods and systems for artifact correction in multi-energy imaging/spectral radiography is needed.

SUMMARY

According to an aspect of the present specification, it provides a method for correcting projection data. The method includes: obtaining transform projection data and entity projection data related to the imaging object, the transform projection data includes the first projection data related to the pixel shading generated by the detector components; inputting the entity projection data, the transform projection data to the trained correction model and obtaining the correction projection data.

According to another aspect of the present specification, it provides a system for correcting projection data. The system includes: data obtaining module, configured to obtain the transform projection data and the entity projection data related to the imaging object, the transform projection data includes the first projection data related to the pixel shading generated by the detector components; correction module, configured to put the entity projection data and the transform data into a trained correction model and obtain the correction projection data.

According to another aspect of the present specification, it provides a device for correcting projection data, including a processor, the processor is configured to execute the method for correcting projection data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further describable in terms of exemplary embodiments. These exemplary embodiments are describable in detail with reference to the drawings. These embodiments are non-limiting exemplary embodiments, in which like reference numerals represent similar structures throughout the several views of the drawings, and wherein.

DETAILED DESCRIPTION

Figure 1:
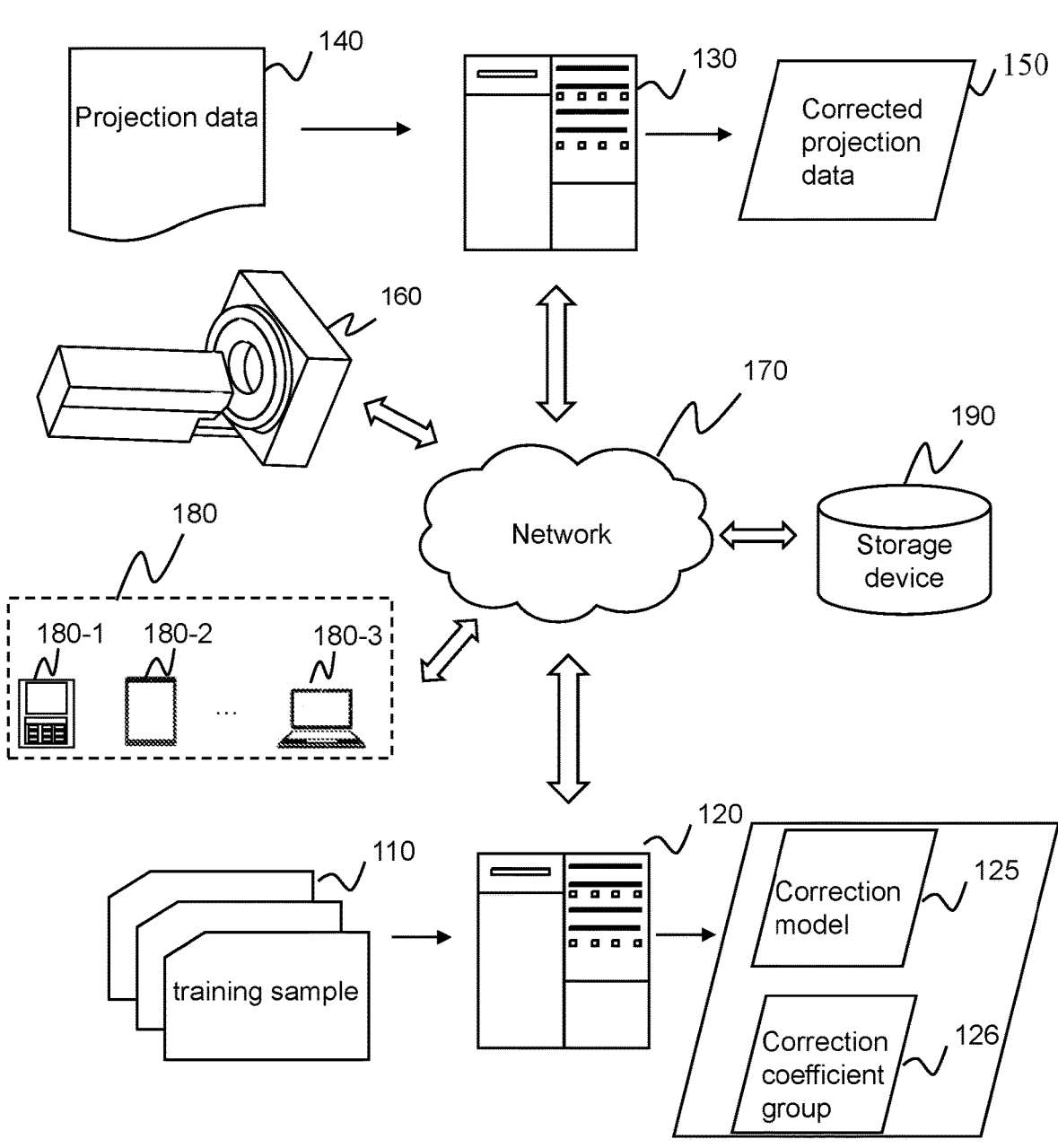
FIG. 1 is a schematic diagram illustrating an exemplary system for correcting projection data according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been describable at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assemblies of different levels in ascending order. However, the terms may be displaced by other expressions if they achieve the same purpose.

Generally, the word "module," "unit," or "block," as used herein, refers to logic embodied in hardware or firmware, or to a collection of software instructions. A module, a unit, or a block describable herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality describable herein may be implemented as software modules/units/blocks, but may be represented in hardware or firmware. In general, the modules/units/blocks describable herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure provides methods and systems for artifact correction in multi-energy imaging/spectral radiography. The methods may include obtaining raw projection data and transformed projection data determined based on the raw projection data. In some embodiments, the raw projection data may be obtained by scanning an object using an imaging device. The transformed projection data may include at least one of: first projection data relating to radiation obstructed by the imaging device, or a portion thereof, second projection data relating to a position of a detector, or a portion thereof, or at least one term of an N-th power of a polynomial representation of the raw projection data, wherein N is an integer greater than or equal to 2. The methods may further include obtaining corrected projection data by processing the raw projection data and the transformed projection data using a correction model such that the quality of an image reconstructed based on the corrected projection data can be improved.

In some embodiments, by including the first projection data relating to radiation obstructed by the imaging device, or a portion thereof, in the input to the correction model, a correction with respect to an artifact (also referred to as first artifact) due to an obstructed ray by the imaging device, or a portion thereof (the detector, or a portion thereof), in the raw projection data and ultimately in an image determined based on the raw projection data may be achieved. In some embodiments, by including the second projection data relating to a position of the detector, or a portion thereof, in the input to the correction model, a correction with respect to an artifact (also referred to as second artifact) due to a deviation of an actual position of the detector, or a portion thereof from a reference position (e.g., an ideal or intended position), in the raw projection data and ultimately in an image determined based on the raw projection data may be achieved. In some embodiments, by including the at least one term of the N-th power of the polynomial representation of the raw projection data in the input to the correction model, a correction with respect to a multi-energy artifact due to beam hardening in the raw projection data and ultimately in an image determined based on the raw projection data may be achieved. By taking into consideration of the influence of radiation obstructed by the imaging device, or a portion thereof, the position of the detector, or a portion thereof on the raw projection data, and/or the beam hardening on the raw projection data, the quality of the projection data correction may be improved, and in turn a quality of an image based on the corrected projection data may also be improved.

FIG. 1 is a schematic diagram illustrating an exemplary system 100 for correcting projection data according to some embodiments of the present disclosure. As shown in FIG. 1, the system 100 may include a first processing device 130, a second processing device 120, an imaging device 160, a network 170, one or more terminals 180, and a storage device 190. The components in the system 100 may be connected in one or more of various ways. Merely by way of example, as illustrated in FIG. 1, the imaging device 160 may be connected to the first processing device 130 and/or the second processing device 120 through the network 170. As another example, the imaging device 160 may be connected to the first processing device 130 and/or the second processing device 120 directly. As a further example, the storage device 190 may be connected to the first processing device 130 and/or the second processing device 120 directly or through the network 170. As still a further example, one or more terminals 180 may be connected to the first processing device 130 and/or the second processing device 120 directly or through the network 170.

In multi-energy imaging radiography (or referred to as multi-energy imaging), as rays emitted by an imaging device are polychromatic, beam hardening may occur. That is, when a polychromatic ray transmits through a material (e.g., a tissue, an organ, etc.), the relationship between the attenuation and material thickness may deviate from linearity, due at least in part to low-energy photons within the polychromatic ray being absorbed more than high-energy photons within the ray, thereby causing the ray to become progressively harder as the ray transmits through the material. Beam hardening may result in a deviation of the raw projection data from raw projection data obtained based on imaging using a monochromatic ray (or referred to as ideal raw projection data) when there is no or negligible beam hardening, and in turn be reflected as a multi-energy artifact in the image reconstructed based on the raw projection data. In some embodiments, one or more artifacts may be generated by a component of the imaging device (e.g., a detector, or a portion thereof). For example, a detector, or a portion thereof, may obstruct received rays during a scanning process, causing a defect in the raw projection data, which may be reflected as an artifact in an image reconstructed based on the raw projection data. As another example, an actual position of the detector, or a portion thereof may deviate from a reference position (e.g., an ideal or intended position), causing a defect in the raw projection data, which may be reflected as an artifact in an image reconstructed based on the raw projection data. In some embodiments, the system 100 may be configured to correct a multi-energy ray artifact generated by an imaging device employing a multi-energy ray, and/or correct artifact(s) generated due to one or more factors involving the imaging device, or a portion thereof, for example, a detector.

The imaging device 160 may generate or provide image data by scanning an object, or at least a part of the object. Exemplary imaging devices may include an X-ray scanning device, a computed tomography (CT) device (e.g., a multi-energy CT scanner), a positron emission tomography-computed tomography (PET-CT) device, a laser scanning device, or the like, or any combination thereof. In some embodiments, the imaging device may include a CT device, e.g., a multi-energy CT scanner. The multi-energy CT scanner may be configured to emit a multi-energy ray for multi-energy imaging of the object. In some embodiments, the multi-energy CT scanner may be configured to emit a single energy ray for single energy imaging of the object.

In some embodiment, the imaging device 160 may include a detector. The detector may receive a radiation ray (e.g., a multi-energy ray, a single energy ray) and generate electrical signals. In some embodiments, the detector may include an anti-scatter grid (ASG), a butterfly filter, or the like, or any combination thereof.

The first processing device 130 and the second processing device 120 may be the same or different. The first processing device 130 or the second processing device 120 refers to a system with a computing capability. The first processing device 130 or the second processing device 120 may include one or more computers, such as a server, a personal computer, or a computing platform including multiple computers connected in any one of suitable structures.

In some embodiments, the processing device 130 or the second processing device 120 may process data and/or information obtained from the imaging device 160, the storage device 190, and/or the terminal(s) 180.

The second processing device 120 may be configured to determine a correction model 125 by training a preliminary correction model using the plurality of training samples 110. More descriptions regarding the training process of the correction model may be found elsewhere in the present disclosure. See, e.g., FIGS. 4 and 5, and relevant descriptions thereof.

The first processing device 130 may be configured to perform one or more operations of a process for correcting projection data, more descriptions of which may be found elsewhere in the present disclosure. See, e.g., FIG. 3, and the description thereof. In some embodiments, the first processing device 130 may obtain corrected projection data 150 by processing the projection data 140 using the correction model 125.

The first processing device 130 or the second processing device 120 may include a processor that may execute program instructions. The processor may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The first processing device 130 or the second processing device 120 may include storage media that may store instructions or data. The storage media may include a mass storage device, a removable storage device, a volatile read-and-write memory, a read-only memory (ROM), or the like, or any combination thereof.

The network 170 may include any suitable network that can facilitate the exchange of information and/or data for the system 100. In some embodiments, one or more components of the system 100 (e.g., the imaging device 160, the first processing device 130, the second processing device 120, the storage device 190, the terminal(s) 180, etc.) may communicate information and/or data with one or more other components of the system 100 via the network 170. For example, the first processing device 130 may obtain data (e.g., raw projection data) from the imaging device 160 via the network 170. As another example, the first processing device 130 may obtain user instruction(s) from the terminal(s) 140 via the network 170. The network 170 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, server computers, or the like, or a combination thereof. For example, the network 170 may include a wireline network, an optical fiber network, a telecommunication network, a local area network, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 170 may include one or more network access points. For example, the network 170 may include wired and/or wireless network access points such as base stations and/or internet exchange points, through which one or more components of the system 100 may be connected to the network 170 to exchange data and/or information.

The storage device 190 may store data, instructions, and/or any other information. In some embodiments, the storage device 190 may store data obtained from the imaging device 110, the first processing device 130, the second processing device 120, and/or the terminal(s) 180. In some embodiments, the storage device 190 may store data and/or instructions that the first processing device 130 or the second processing device 120 may execute or use to perform exemplary methods described in the present disclosure. In some embodiments, the storage device 190 may include a mass storage device, a removable storage device, a volatile read-and-write memory, a read-only memory (ROM), or the like, or any combination thereof. In some embodiments, the storage device 190 may be implemented on a cloud platform as described elsewhere in the disclosure. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 190 may be connected to the network 170 to communicate with one or more other components in the system 100 (e.g., the first processing device 130, the second processing device 140, the terminal(s) 180, etc.). One or more components in the system 100 may access the data or instructions stored in the storage device 190 via the network 170. In some embodiments, the storage device 190 may be part of the first processing device 130 or second processing device 120.

The terminal(s) 180 may be connected to and/or communicate with the imaging device 160, the first processing device 130, the second processing device 120, and/or the storage device 190. For example, the terminal(s) 180 may obtain a corrected image generated based on corrected projection data from the first processing device 130. In some embodiments, the terminal(s) 180 may include a mobile device 180-1, a tablet computer 180-2, a laptop computer 180-3, or the like, or any combination thereof. For example, the mobile device 180-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 180 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input device may include a text scanning device. The input information received through the input device may be transmitted to the first processing device 130 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 180 may be part of the first processing device 130 or the second processing device 120.

In some embodiments, the system 100 may omit the second processing device 120. For example, the first processing device 130 may generate a correction model by using a plurality of training samples, and apply the correction model in, for example, generating corrected projection data. In some embodiments, the correction model may be generated by a processing device of a system other than the system 100. For instance, the correction model may be generated by a first system of a vendor who provides and/or maintains such model, while the generation of the corrected projection data using the provided model may be performed on a second system of a client of the vendor. In some embodiments, the application of the model may be performed online in response to a request for, for example, generating the corrected projection data. In some embodiments, the model may be generated offline.

It should be noted that the above description of the system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the system 100 may include one or more additional components. Alternatively or additionally, one or more components of the system 100, such as the storage device 190 described above may be omitted. As another example, two or more components of the imaging system 100 may be integrated into a single component.

Figure 2A:
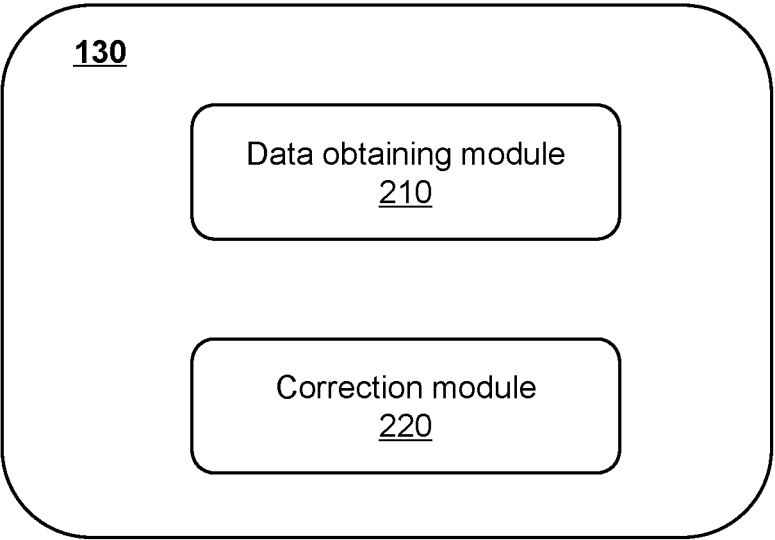
FIGS. 2A and 2B are block diagrams illustrating an exemplary first processing device configured to correct projection data and an exemplary second processing device configured to generate a correction model according to some embodiments of the present disclosure, respectively.
Figure 2B:
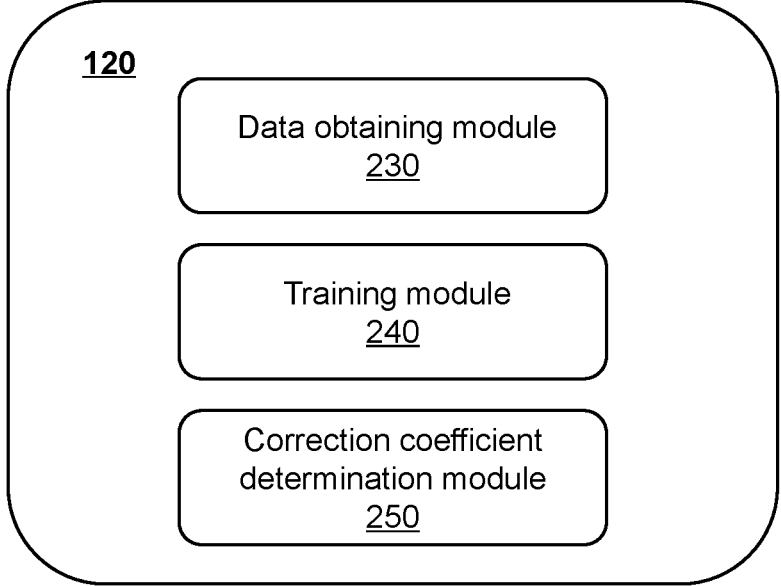

FIG. 2A is a block diagram illustrating an exemplary first processing device 130 configured to correct projection data according to some embodiments of the present disclosure. FIG. 2B is a block diagram illustrating an exemplary second processing device 120 configured to generate a correction model according to some embodiments of the present disclosure.

As illustrated in FIG. 2A, the first processing device 130 may include a data obtaining module 210 and a correction module 220.

In some embodiments, the data obtaining module 210 may be configured to obtain raw projection data and transformed projection data determined based on the raw projection data. The raw projection data may be obtained by scanning an object using an imaging device. The transformed projection data may include at least one of: first projection data relating to radiation obstructed by the imaging device, or a portion thereof, second projection data relating to a position of the detector, or a portion thereof, or at least one term of an N-th power of a polynomial representation of the raw projection data, wherein N is an integer greater than or equal to 2.

In some embodiments, the data obtaining module 210 may be configured to determine the first projection data based on exponential transformation of the raw projection data. The data obtaining module 210 may be configured to determine the second projection data based on gradient information of the raw projection data. The gradient information may relate to the position of the detector, or a portion thereof. The data obtaining module 210 may be configured to obtain the second projection data by performing a differential operation on the raw projection data based on the position of the detector, or a portion thereof.

In some embodiments, the correction module 220 may be configured to obtain corrected projection data by processing the raw projection data and the transformed projection data using a correction model. The correction model may include a trained machine learning model. In some embodiments, the correction module 220 may be configured to obtain corrected projection data by processing the raw projection data and the transformed projection data based on a correction coefficient group. For example, the correction module 220 may perform polynomial fitting of the raw projection data and the transformed projection data based on the correction coefficient group to provide the corrected projection data. In some embodiments, the correction module 220 may be configured to determine, based on the input including the raw projection data and the transformed projection data, the corrected projection data without involving the determination of a correction coefficient group.

As illustrated in FIG. 2B, the second processing device 120 may include a data obtaining module 230, a training module 240, and a correction coefficient determination module 250. In some embodiments, the data obtaining module 230 may be configured to obtain a plurality of training samples. In some embodiments, each of the plurality of training samples may include sample raw projection data, sample transformed projection data obtained based on the sample raw projection data, and standard projection data of a sample standard energy ray corresponding to the sample raw projection data. The training module 240 may be configured to determine the correction model by training a preliminary correction model using the plurality of training samples. In some embodiments, the correction coefficient determination module 250 may be configured to determine a correction coefficient group based on the correction model. In some embodiments, the correction coefficient group may be configured to determine the corrected projection data.

It should be noted that the above descriptions are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the first processing device 130 and/or the second processing device 120 may share two or more of the modules, and any one of the modules may be divided into two or more units. In some embodiments, the first processing device 130 and/or the second processing device 120 may include one or more additional modules, such a storage module (not shown) for storing data. In some embodiments, the first processing device 130 and the second processing device 120 may be integrated into one processing device. In some embodiments, the first processing device 120 may further include an image reconstruction module configured to generate an image based on the corrected projection data. In some embodiments, the correction coefficient determination module 250 may be omitted from the second processing device 120, and the correction model may be configured to determine, based on the input including the raw projection data and the transformed projection data, the corrected projection data without involving the determination of a correction coefficient group.

Figure 3:
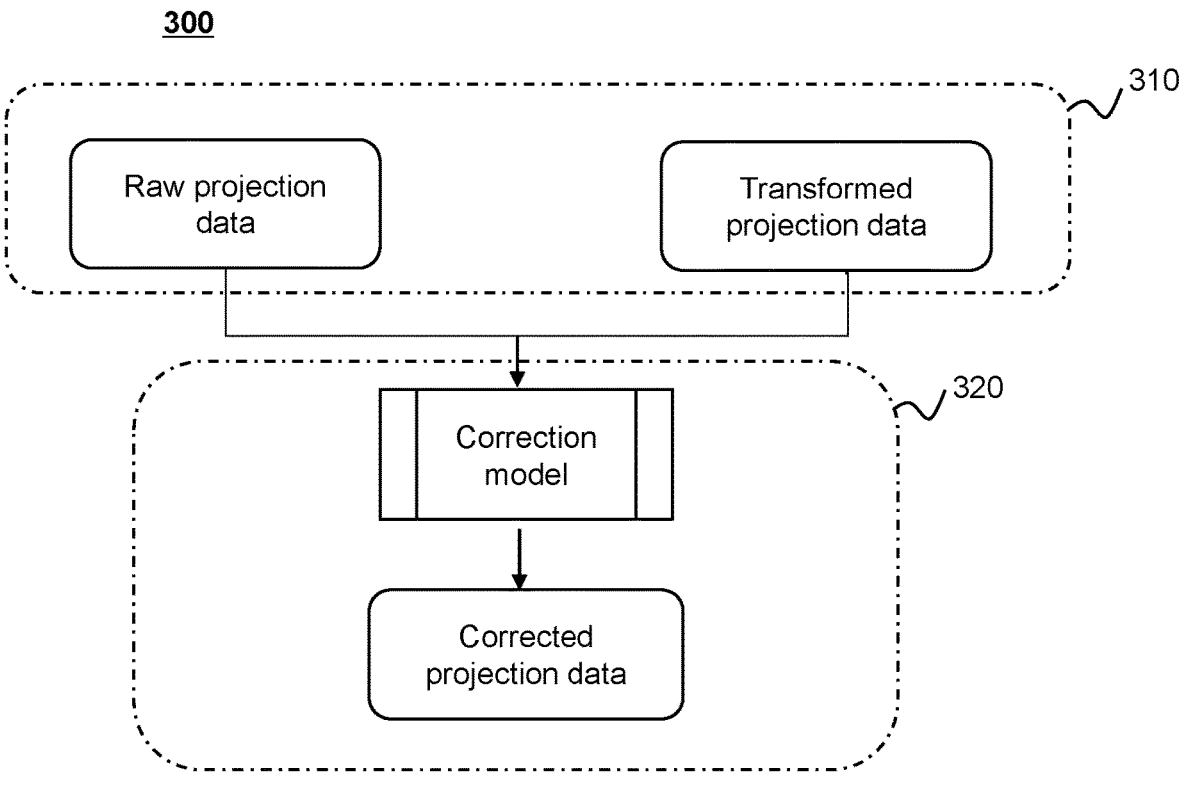
FIG. 3 is a flowchart illustrating an exemplary process for correcting projection data according to some embodiments of the present disclosure.

FIG. 3 is a flowchart illustrating an exemplary process for correcting projection data according to some embodiments of the present disclosure. In some embodiments, process 300 may be executed by the system 100. For example, the process 300 may be implemented as a set of instructions (e.g., an application) stored in a storage medium. In some embodiments, a processor of the system 100 (e.g., the processor of the first processing device 130) may execute the set of instructions and may accordingly be directed to perform the process 300.

In 310, raw projection data and transformed projection data may be obtained. In some embodiments, 310 may be executed by the first processing device 130 (e.g., the data obtaining module 210 implemented on the first processing device 130). In some embodiments, the transformed projection data may be determined based on the raw projection data.

As used herein, raw projection data refers to projection data obtained by scanning an object using an imaging device. In some embodiments, the raw projection data (e.g., the projection data 140 in FIG. 1) may be acquired using the imaging device, such as the imaging device 160 of the system 100. The imaging device may include, for example, a CT device (e.g., a multi-energy CT scanner), an X-ray scanning device, a PET-CT device, a laser scanning device, or the like, or any combination thereof. The imaging device may be configured to emit radiation rays for imaging an object.

In some embodiments, the imaging device may include one or more detectors. A detector may receive at least a portion of the polychromatic rays emitted by the imaging device that have traversed an object which in turn may provide raw projection data. For example, when the imaging device includes a CT device, the raw projection data of the object may be denoted as p.

The object may be a physical object that may be scanned and imaged, such as a phantom, a human body, an animal, a plant, goods, or a portion thereof, etc. The way of scan may include a general scan, a special scan, etc. In some embodiments, the general scan may include a transverse scan, a coronary scan, etc. In some embodiments, the special scan may include a positioning scan, a thin-layer scan, a magnification scan, a target scan, a high-resolution scan, etc. In some embodiments, the positioning scan may be performed to identify a region of interest (ROI), or a portion (e.g., an organ) of an object. In some embodiments, the imaging device may scan the object from different angles at multiple time points to obtain scanning data from different perspectives. In some embodiments, the imaging device may scan the object by using a multi-energy ray (or referred to as a polychromatic ray) or a single-energy ray. As used herein, a multi-energy ray refers to a ray with a variety of energies of an energy distribution. For example, a multi-energy ray may be a ray with energies of 60 to 100 keV. As used herein, a single-energy ray refers to a ray with an energy. For example, a single-energy ray may be a ray with an energy of 60 keV. In some embodiments, the imaging device may include a multi-energy CT scanner. The multi-energy CT scanner may be configured to emit a multi-energy ray for multi-energy imaging of the object.

In some embodiments, the raw projection data may include projection data obtained by multi-energy imaging of an object using the multi-energy CT scanner. As in the multi-energy imaging radiography, the emitted rays may be polychromatic, and beam hardening may occur during the ray transmission process, resulting in a deviation of the raw projection data from the ideal raw projection data obtained when there is no or negligible beam hardening, and further causing a beam hardening artifact (or referred to as multi-energy ray artifact) in an image obtained by image reconstruction based on the affected raw projection data. The defect of the raw projection data due to beam hardening may be referred to as a third defect of the raw projection data for brevity.

In some embodiments, the raw projection data may be obtained from the imaging device. The raw projection data may be transmitted to the first processing device 130 from the imaging device via a wired connection, a wireless connection, or a combination thereof. For example, the first processing device 130 (e.g., a processor) may obtain the raw projection data from the imaging device according to an instruction. As another example, the imaging device may transmit the raw projection data to the first processing device 130 according to an instruction. In some embodiments, the raw projection data may be obtained from a storage device (e.g., a storage media of the first processing device 130, the storage device 190). For example, a database may be implemented in the storage device for storing data. The raw projection data generated by the imaging device may be transferred to the first processing device 130 and stored in the database. The first processing device 130 may obtain the raw projection data from the database.

As used herein, the transformed projection data refers to derived projection data obtained by transforming the raw projection data. The transformed projection data may include at least one of first projection data relating to radiation obstructed by the imaging device, or a portion thereof, second projection data relating to a position of the detector, or a portion thereof, or at least one term of an N-th power of a polynomial representation of the raw projection data, or the like, or any combination thereof. N may be an integer greater than or equal to 2.

In some embodiments, the transformed projection data may include the first projection data relating to radiation obstructed by the imaging device, or a portion thereof.

When the imaging device emits radiation rays toward the object for imaging, at least a portion of the emitted radiation rays may be obstructed by the imaging device, or a portion thereof. In some embodiments, at least a portion of the radiation rays may be obstructed by one or more components of the imaging device, e.g., an anti-scatter grid (ASG), a butterfly filter, a collimator, or the like, or a portion thereof, or any combination thereof. The obstructed radiation ray(s) may not be properly detected by the detector. For instance, the obstructed radiation ray(s) may be completely blocked (e.g., deflected, absorbed) by the one or more components of the imaging device and therefore not detected by the detector at all. As another example, in addition to attenuation by the object through which the obstructed ray(s) traverses, the obstructed radiation ray(s) may be further attenuated by the one or more components of the imaging device, and therefore the intensity of the obstructed ray(s) detected by the detector is lower than it should be. Such a radiation obstruction may cause a defect in the obtained raw projection data. The defect may represent a deviation of the raw projection data from raw projection data obtained when there is no obstruction by the imaging device, or a portion thereof. The defect in the raw projection data in this case may be also referred to as a first defect of the raw projection data for brevity. The first defect of the raw projection data may result in an artifact on an image generated based on the raw projection data, making the image inaccurate. In some embodiments, the radiation obstruction may occur when one or more components of the imaging device tilt, deform, or deviate from one or more reference positions (e.g., an installation position, an intended position). In some embodiments, the radiation obstruction may occur because of a characteristic of each of the one or more components of the imaging device e.g., the thickness of the grid sheet of the ASG, the volume of the collimator, the volume of the butterfly filter, etc.

In some embodiments, the first projection data may relate to the radiation obstruction. In some embodiments, the first projection data may be determined based on the raw projection data and the radiation obstruction. For example, the first projection data may be determined based on the exponential transformation of the raw projection data. Assuming that the raw projection data is expressed as the projection value p, an exponential transformation may be performed on the projection value p to obtain the transformed projection value, denoted as exp(–p). The exp(–p) may be designated as the first projection data. By performing an exponential transformation on the raw projection data, the raw projection data may be converted from projection domain to intensity domain, thereby delineating the effect of the radiation obstruction on the raw projection data.

In some embodiments, the transformed projection data may include second projection data relating to a position of the detector, or a portion thereof.

The position of the detector, or a portion thereof may refer to an actual position where the detector is installed or when the imaging device including the detector operates. The actual position of the detector, or a portion thereof may deviate from a reference position (e.g., an ideal or intended position) of the detector, or a portion thereof. Merely by way of illustration, a deviation of the position of a detector from its reference position may be due to one or more factors including, e.g., an error in installation, a move of the detector in an operation of the imaging device, or the like, or a combination thereof. When the imaging device scans the object, the deviation of the position of the imaging device, or a portion thereof from its reference position may influence the raw projection data, bringing a defect to the raw projection data. The defect in the raw projection data in this case may be also referred to as a second defect of the raw projection data for brevity.

In some embodiments, the second projection data may be determined based on the raw projection data and the position of the detector, or a portion thereof. In some embodiments, the second projection data may be determined based on gradient information of the raw projection data. The gradient information may relate to the position of the detector, or a portion thereof. In some embodiments, the second projection data may be obtained by performing a differential operation on the raw projection data. For example, if the raw projection data is expressed as the projection value p, the second projection data may be obtained by performing a differential operation on the projection value p. The second projection data may be denoted as dp/dx. The second projection data may reflect an influence of the position of the detector, or a portion thereof on the raw projection data.

In some embodiments, the transformed projection data may include at least one term of an N-th power of a polynomial representation of the raw projection data, or the like, or any combination thereof. N may be an integer greater than or equal to 2.

Assuming that the raw projection data is expressed as the projection value p, at least one term of the N-th power of the polynomial representation of the raw projection data may be denoted as $p^2$, $p^3$, . . . , $p^N$, or the like, or any combination thereof. The at least one term of the N-th power of the polynomial representation of the raw projection data may be used as part of the transformed projection data to correct multi-energy ray artifact based on a polynomial fitting process of the raw projection data.

In 320, corrected projection data may be obtained by processing the raw projection data and the transformed projection data using a correction model. In some embodiments, 320 may be executed by the first processing device 130 (e.g., the correction module 220 implemented on the first processing device 130).

As used herein, the corrected projection data refers to projection data obtained by correcting the raw projection data. In some embodiments, the corrected projection data (e.g., the corrected projection data 150 in FIG. 1) may be determined by inputting the raw projection data and the transformed projection data into the correction model (e.g., the correction model 125 in FIG. 1). By using both the transformed projection data and raw projection data as an input of the correction model, the effect of correcting the raw projection data can be improved compared to only using the raw projection data as input into the correction model.

In some embodiments, by including the first projection data relating to radiation obstructed by the imaging device, or a portion thereof, in the input to the correction model, a correction with respect to an artifact (also referred to as first artifact) due to an obstructed ray by the imaging device, or a portion thereof, in the raw projection data and ultimately in an image determined based on the raw projection data may be achieved. In some embodiments, by including the second projection data relating to a position of the detector, or a portion thereof, in the input to the correction model, a correction with respect to an artifact (also referred to as second artifact) due to a deviation of an actual position of the detector, or a portion thereof from a reference position (e.g., an ideal or intended position), in the raw projection data and ultimately in an image determined based on the raw projection data may be achieved. In some embodiments, by including the at least one term of the N-th power of the polynomial representation of the raw projection data in the input to the correction model, a correction with respect to a multi-energy artifact due to beam hardening in the raw projection data and ultimately in an image determined based on the raw projection data may be achieved.

In some embodiments, the input of the correction model may include a constant, for example, a constant f. For example, the constant input to the correction model may be used to represent a value of a baseline of the imaging device, or a portion thereof (e.g., the detector) when there is no radiation emitted by the imaging device for imaging purposes that impinges on the detector. In some embodiments, the constant may be determined by testing the imaging device or the detector or from product specifications of the imaging device or the detector provided by, e.g., the manufacturer of the imaging device or the detector. For example, the detector may be tested to obtain the value of the baseline of the detector when the imaging device emits no radiation for imaging. The value of the baseline may be used as the constant input to the model. In some embodiments, the constant may be used as an additional offset for the correction model, thereby further improving the correction effect of the correction model.

The correction model may be obtained by a training process. In some embodiments, the correction model may be determined by training a preliminary correction model using a plurality of training samples (e.g., the training samples 110 in FIG. 1). More descriptions regarding the determination of the correction model may be found elsewhere in the present disclosure. See, e.g., FIG. 4, and relevant descriptions thereof. More descriptions regarding an exemplary correction model may be found elsewhere in the present disclosure. See, e.g., FIG. 5, and relevant descriptions thereof. In some embodiments, the correction module 220 may retrieve the correction model from the storage device 190 or another storage device. For example, the correction model may be obtained by training a preliminary correction model online or offline using the second processing device 120. The second processing device 120 may store in the correction model in the storage device 150 or another storage device. The first processing device 130 may retrieve the correction model from the storage device 150 or another storage device in response to receipt of a request for data correction.

In some embodiments, the corrected projection data may be used to reconstruct an image, for example, a CT image of a scanned object. It should be understood that the image reconstructed based on the corrected projection data may be an image from which artifact(s) (for example, multi-energy ray artifact(s)) have been corrected. In some embodiments, various image reconstruction algorithms may be used to reconstruct an image based on the corrected projection data. Exemplary image reconstruction algorithms may include a back-projection algorithm, an iterative reconstruction algorithm, a filtered back-projection algorithm, Fourier transform algorithm, or the like, or any combination thereof.

In some embodiments, the corrected projection data may be determined based on a correction coefficient group (e.g., the correction coefficient group 126 in FIG. 1). The correction coefficient group may include at least one correction coefficient configured to modulate different portions of the raw projection data and the transformed projection data. The correction coefficient group may be determined based on one or more parameters determined from the correction model obtained described in FIG. 4. Exemplary parameters of the correction model may include a weight, a bias (or referred to as a bias term), a convolution kernel, or the like, or any combination thereof. In some embodiments, the correction coefficient group may include a weight corresponding to each input of the correction model. More description regarding the determination of the correction coefficient may be found elsewhere in the present disclosure. See, e.g., 420, and relevant descriptions thereof.

In some embodiments, the correction coefficient group may be used for polynomial fitting of the raw projection data and the transformed projection data to determine the corrected projection data. The polynomial fitting of the raw projection data and the transformed projection data means inputting the raw projection data and the transformed projection data into an equation (e.g., the equations (1) and (2)) to obtain a calculation result. For example, the corrected projection data may be determined based on an equation as follows:

$$P' = a*p + b*p^2 + c*p^3 + d*\exp^{-p} + e*\frac{dp}{dx}, \tag{1}$$

where p denotes the raw projection data, $p^2$ and $p^3$ denotes the terms of the N-th power of the polynomial representation of the raw projection data, $\exp^{-p}$ denotes the first projection data, $$\frac{dp}{dx}$$

denotes the second projection data, P' denotes the corrected projection data, and a, b, c, d, and e denote the correction coefficients of the raw projection data, the first projection data, and the second projection data, and terms of the N-th power of the polynomial representation of the raw projection data, respectively. The correction coefficients a, b, c, d, and e may be determined based on weights of the correction model represented by the equation (4) described in FIG. 4. As another example, the corrected projection data may be determined based on an equation as follows:

$$P' = a*p + b*\exp^{-p} + c*\frac{dp}{dx}, \tag{2}$$

where p denotes the raw projection data, $\exp^{-p}$ denotes the first projection data, $$\frac{dp}{dx}$$

denotes the second projection data, P′ denotes the corrected projection data, and a, b, and c denote correction coefficients of the raw projection data, the first projection data, and the second projection data, respectively. The correction coefficients a, b, and c may be determined based on weights of the correction model represented by the equation (3) described in FIG. 4.

It should be noted that the above description of the process 300 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 4:
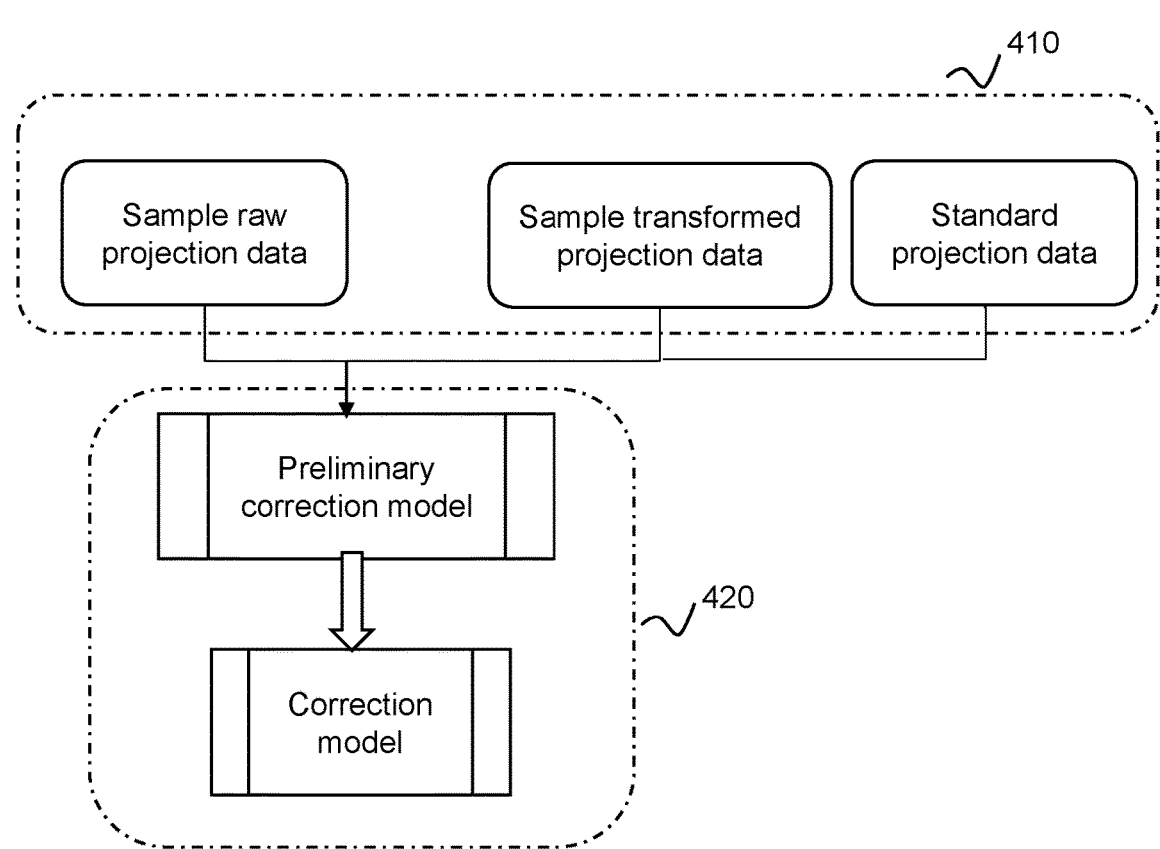
FIG. 4 is a flowchart illustrating an exemplary process for training a preliminary correction model according to some embodiments of the present disclosure.

FIG. 4 is a flowchart illustrating an exemplary process for training a preliminary correction model according to some embodiments of the present disclosure. In some embodiments, process 400 may be executed by the system 100. For example, the process 400 may be implemented as a set of instructions (e.g., an application) stored in a storage medium. In some embodiments, a processor of the system 100 (e.g., the processor of the second processing device 120) may execute the set of instructions and may accordingly be directed to perform the process 400.

In 410, a plurality of training samples may be obtained. In some embodiments, 410 may be executed by the second processing device 120 (e.g., the data obtaining module 230 implemented on the second processing device 120).

Each of the training samples may include sample raw projection data, sample transformed projection data, and standard projection data of a sample standard energy ray. The standard projection data may correspond to the sample raw projection data. For example, the standard projection data may be obtained by a single energy imaging of a sample object, and the sample raw projection data may be obtained by a multi-energy of the same sample object. The sample transformed projection data may be obtained based on the sample raw projection data. In some embodiments, the training samples may be obtained from the imaging device 160 or retrieved from a storage device (e.g., the storage device 190, an external data source), the terminal(s) 180, or any other storage device.

The sample raw projection data refers to sample data of the raw projection data. In some embodiments, the sample raw projection data may be obtained by scanning a sample object using the imaging device. In some embodiments, the sample object may be, for example, a phantom. The phantom refers to a specially designed object used to simulate a living object (e.g., a patient, an animal). The radiation absorption effect or radiation scattering effect of the phantom may be substantially the same as the living object (e.g., the object in FIG. 3). In some embodiments, the phantom may be a non-metallic material or a metallic material. Exemplary metallic materials may include copper, iron, nickel, alloy, etc. Exemplary non-metallic materials may include organic material, inorganic material, etc. In some embodiments, the sample raw projection data may be obtained by a multi-energy imaging of the sample object using the imaging device (e.g., multi-energy CT scanner). In some embodiments, the sample raw projection data may be obtained by a simulation process (for example, a simulation of the sample object). In some embodiments, the sample raw projection data may be obtained by simulation by adding one or more types of defects (e.g., at least one of the first defect, the second defect, or the third defect described elsewhere in the present disclosure) to the standard projection data of a sample standard energy ray. In some embodiments, the sample raw projection data may be obtained by retrieving historical scanning data from the imaging device or the storage device 190.

Sample transformed projection data of a training sample may include transformed project data derived from the sample raw projection data of the training sample. The sample transformed projection data may be determined similar to how the transformed projection data is determined based on raw projection data as described in FIG. 3, the description of which is not repeated here. The sample transformed projection data may include sample first projection data, sample second projection data, or at least one term of an N-th power of a polynomial representation of the sample raw projection data, or the like, or any combination thereof. N may be an integer greater than or equal to 2.

The sample first projection data may reflect a defect caused by radiation obstructed by at least a portion of the imaging device where the sample raw projection data of a training sample is acquired. In some embodiments, the sample first projection data may be obtained by processing the sample raw projection data. In some embodiments, the sample first projection data may be determined based on the exponential transformation of the sample raw projection data in a similar manner as the first projection data, the description of which is not repeated here. See, e.g., 310 and relevant descriptions thereof.

The sample second projection data may reflect a defect due to a deviation of the position of the detector, or a portion thereof, from its reference position where the sample raw projection data of a training sample is acquired. In some embodiments, the sample second projection data may be obtained by processing the sample raw projection data. In some embodiments, the sample second projection data may be determined based on gradient information of the sample raw projection data. For example, the sample second projection data may be obtained by performing a differential operation on the sample raw projection data. In some embodiments, the sample second projection data may be determined in a similar manner as the second projection data, which is not repeated herein. See, e.g., 310 and relevant descriptions thereof.

A sample standard energy ray refers to an energy ray without bringing a multi-energy ray artifact in an image. The standard projection data may include projection data obtained by a standard energy imaging of an object (such as the sample object) using the imaging device. In some embodiments, the sample standard energy ray may include a single energy ray. For example, a single-energy ray may be a ray with an energy of 60 keV while the multi-energy ray may be a ray with energies of 60 to 100 keV. The standard projection data may correspond to the sample raw projection data. In some embodiments, the standard projection data may be obtained by simulating the sample raw projection data. For example, the standard projection data may be obtained by polynomial fitting of the sample raw projection data. In some embodiments, the standard projection data corresponding to the sample raw projection data may be obtained by a single energy imaging of the sample object using the imaging device. During the training process, the standard projection data may be used as a label of a training sample including the sample raw projection data and the sample transformed projection data to effectively correct the third defect of the raw projection data.

In some embodiments, the standard projection data may include projection data obtained by a standard energy imaging of an object (such as the sample object) using an imaging device which has been calibrated. In some embodiments, the calibration of the imaging device may include correcting the first defect due to radiation obstruction by an imaging device, or a portion thereof and/or the second defect due to a position of a detector of the imaging device by manually correction or other correction processes. During the training process, the standard projection data may be used as a label of a training sample including the sample raw projection data and the sample transformed projection data to effectively correct the first defect and/or the second defect of the raw projection data.

In 420, the correction model may be determined by training a preliminary correction model using the plurality of training samples. In some embodiments, 420 may be executed by the second processing device 120 (e.g., the training module 240 implemented on the second processing device 120).

In some embodiments, the preliminary correction model may include a machine learning model that has not been trained using any training samples. In some embodiments, the preliminary correction model may include a pre-trained machine learning model that may be trained using a training set. Training data in the training set may be partially or entirely different from the plurality of training samples obtained in 410. For example, the pre-trained machine learning model may be provided by a system of a vendor who provides and/or maintains such a pre-trained machine learning model.

In some embodiments, the preliminary correction model may be constructed based on a neural network model. Exemplary neural network models may include a deep neural network model. The deep neural network model may include, for example, a recurrent neural network (RNN) model, a deep feedforward (DFF) network model, a fully connected neural network (DNN) model, etc.).

In some embodiments, the preliminary correction model may include a multi-layer structure. For example, the preliminary correction model may include an input layer, an output layer, and one or more hidden layers (e.g., 1, 2, 3, etc.) between the input layer and the output layer. In some embodiments, the hidden layers may include one or more convolution layers, one or more rectified-linear unit layers (ReLU layers), one or more pooling layers, one or more fully connected layers, or the like, or any combination thereof. As used herein, a layer of a machine learning model refers to an algorithm or a function for processing input data of the layer. Different layers may perform different kinds of processing on their respective input. A successive layer may use output data from a previous layer of the successive layer as input data. In some embodiments, an output of the output layer may include a predicted value, e.g., sample corrected projection data corresponding to a training sample.

In some embodiments, each of the layers may include one or more nodes. In some embodiments, each node may be connected to one or more nodes in a previous layer. The number of nodes in each layer may be the same or different. In some embodiments, each node may correspond to an activation function. In some embodiments, an activation function of a node may define an output of the node given an input or a set of inputs. In some embodiments, each connection between two of the plurality of nodes in the correction model (or the preliminary correction model, or a partially trained correction model) may transmit a signal from one node to another node. In some embodiments, each connection may correspond to a weight. As used herein, a weight corresponding to a connection may be used to increase or decrease the strength or impact of the signal at the connection.

In some embodiments, the preliminary correction model may be trained according to a training algorithm based on the training samples. Exemplary training algorithm may include a gradient descent algorithm, a Newton's algorithm, or the like, or any combination thereof. In some embodiments, the preliminary correction model may be trained by performing a plurality of iterations. Before the plurality of iterations, the parameters of the initial machine learning model may be initialized. For example, the connected weights and/or the bias vector of nodes of the preliminary correction model may be initialized by assigning random values, e.g., a value from −1 to 1. In some embodiments, the parameters of the initial machine learning model may be initialized based on a Gaussian random algorithm, a Xavier algorithm, etc. Then the plurality of iterations may be performed to iteratively update the parameters of the preliminary correction model until a termination condition is satisfied.

In some embodiments, the sample raw projection data and the sample transformed projection data of a training sample may be used as an input of the preliminary correction model, and the standard projection data corresponding to the sample raw projection data and the sample transformed projection data may be used as a label of the input (e.g., a training sample) to train the preliminary correction model.

The termination condition may provide an indication of whether the preliminary correction model is sufficiently trained. For example, the termination condition may be satisfied if the value of a cost function or an error function associated with the preliminary correction model is minimal or smaller than a threshold (e.g., a constant). As another example, the termination condition may be satisfied if the value of the cost function or the error function converges. The convergence may be deemed to have occurred if the variation of the values of the cost function or the error function in two or more consecutive iterations is smaller than a threshold (e.g., a constant). As still another example, the termination condition may be satisfied when a specified number or count of iterations are performed in the training process. For each of the plurality of iterations, each training sample and the corresponding label may be inputted into the preliminary correction model. The sample raw projection data and sample transformed projection data for a training sample may be processed by one or more layers of the preliminary correction model to generate a predicted result (e.g., a predicted corrected projection data) for the inputted training sample. Each of predicted corrected projection data in the inputted training sample may be compared with a desired result (i.e., the label) associated with the training sample based on the cost function or error function of the preliminary correction model. The cost function or error function of the preliminary correction model may be configured to assess a total difference (also referred to as a global error) between a testing value (e.g., the predicted corrected projection data) of the preliminary correction model and a desired value (e.g., the label of the training sample). The total difference may be equal to a sum of multiple differences each of which is between one of the predicted result and the label of the inputted training sample. If the value of the cost function or error function exceeds a threshold in a current iteration, the parameters of the preliminary correction model may be adjusted and/or updated to cause the value of the cost function or error function to reduce to a value smaller than the threshold. Accordingly, in a next iteration, sample raw projection data and sample transformed projection data in another training sample may be inputted into the preliminary correction model to train the preliminary correction model as described above until the termination condition is satisfied.

In some embodiments, the termination condition may be that a value of a cost function or error function in the current iteration is less than a threshold value. In some embodiments, the termination condition may include that a maximum number (or count) of iterations has been performed, that an approximation error is less than a certain threshold, a difference between the values of the cost function or error function obtained in a previous iteration and the current iteration (or among the values of the cost function or error function within a certain number or count of successive iterations) is less than a certain threshold, that a difference between the approximation error at the previous iteration and the current iteration (or among the approximation errors within a certain number or count of successive iterations) is less than a certain threshold. In response to determining that the termination condition is not satisfied, the parameters of the preliminary correction model may be adjusted, and the iterations may continue. For example, the training module 240 may update values of the parameters by performing a backpropagation machine learning training algorithm, e.g., a stochastic gradient descent backpropagation training algorithm. In response to determining that the termination condition is satisfied, the iterative process may terminate and the trained preliminary correction model may be stored and/or output. In some embodiments, after the training process is complete, a validation set may be processed to validate the trained correction model. In some embodiments, the trained preliminary correction model may be stored in a storage device (e.g., the storage device 190), the second processing device 120, the terminal(s) 180, or an external data source.

In some embodiments, during the training process of the preliminary correction model using the standard projection data of a sample standard energy ray (e.g., the single energy ray without bringing a multi-energy ray artifact) of the imaging device as the label corresponding to the sample raw projection data and the sample transformed projection data, the correction model obtained by the training process can effectively correct the third defect of the raw projection data related to the multi-energy ray artifact. In some embodiments, the correction model obtained by the training process can effectively correct the first defect and/or second defect of the raw projection data. By taking into consideration of the first defect due to radiation obstruction by an imaging device, or a portion thereof, and/or the second defect due to a position of a detector, or a portion thereof, by way of, e.g., including the sample first projection data and/or sample second projection data as input in the training process and including the standard projection data of a sample standard energy ray of the calibrated imaging device as the label, the correction model so trained may be configured to further correct the first defect and/or the second defect in raw projection data.

In some embodiments, a correction coefficient group may be determined based on the correction model obtained by the training process. In some embodiments, the correction coefficient group may be determined by the second processing device 120 (e.g., the correction coefficient determination module 250 implemented on the second processing device 120). In some embodiments, the correction coefficient group may be used to correct the first defect of the raw projection data, the second defect of the raw projection data, and/or the third defect of the raw projection data. In some embodiments, the parameter(s) of the correction model may include a weight, a bias vector, a convolution kernel of the correction model, or the like, or any combination thereof.

In some embodiments, the correction coefficient group may include one or more weights of the correction model. Each input of the correction model (such as the raw projection data, the first projection data, the second projection data) may correspond to a weight. In some embodiments, the correction model may be represented by an equation (3):

$$P' = f\left(a*p + b*\exp^{-p} + c*\frac{dp}{dx}\right), \quad (3)$$

where p denotes the raw projection data, $\exp^{-p}$ denotes the first projection data, $$\frac{dp}{dx}$$

denotes the second projection data, P' denotes the corrected projection data, and a, b, and c denote the weights of the raw projection data, the first projection data, and the second projection data, respectively.

In some embodiments, the corrected projection data may be obtained based on the correction model represented by Equation (3). In some embodiments, the weights a, b, and c corresponding to each input of the correction model may be used as correction coefficients of the correction coefficient group. The obtained correction coefficient group may be used in correcting the first defect of raw projection data, and/or second defect of raw projection data.

In some embodiments, the correction model may be represented by an equation (4):

$$P' = f\left(a*p + b*p^2 + c*p^3 + d*\exp^{-p} + e*\frac{dp}{dx}\right) \quad (4)$$

where p denotes the raw projection data, $p^2$ and $p^3$ denotes the terms of the N-th power of the polynomial representation of the raw projection data, $\exp^{-p}$ denotes the first projection data, $$\frac{dp}{dx}$$

denotes the second projection data, P' denotes the corrected projection data, and a, b, c, d, and e denote weights of the raw projection data, two terms, $p^2$ and $p^3$, of the N-th power of the polynomial representation of the raw projection data, the first projection data, and the second projection data, and respectively.

In some embodiments, the corrected projection data may be obtained based on the correction model represented by the equation (4). In some embodiments, the weights a, b, c, d, e corresponding to each input of the correction model may be used as correction coefficients of the correction coefficient group.

In some embodiments, a weight of an item of the input may be determined by setting the other items of the input of the correction model as zero. For example, when the input data includes the raw projection data p, the first projection data exp(−p), and the second projection data dp/dx, the first projection data exp(–p), and the second projection data dp/dx, the first projection data exp(–p), and the second projection data dp/dx, the first projection data $\exp^{-p}$, and the second projection data dp/dx may be set to zero. Thus, the correction model may be expressed as P'=a*p, and the weight a corresponding to p may be obtained. The weight(s) corresponding to other items of the input may be similarly determined.

By determining the correction coefficient group based on the parameters of the correction model, only a small amount of training samples is needed to obtain the correction model. As the amount of data (e.g., weights of the correction model) needed to determine correction coefficient group is relatively small, the correction model may be trained with a small amount of training samples to obtain the stable correction coefficient group. Thus, the artifact(s) described in the present disclosure may be corrected more conveniently without a large amount of training samples.

It should be noted that the above description of the process 400 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 5:
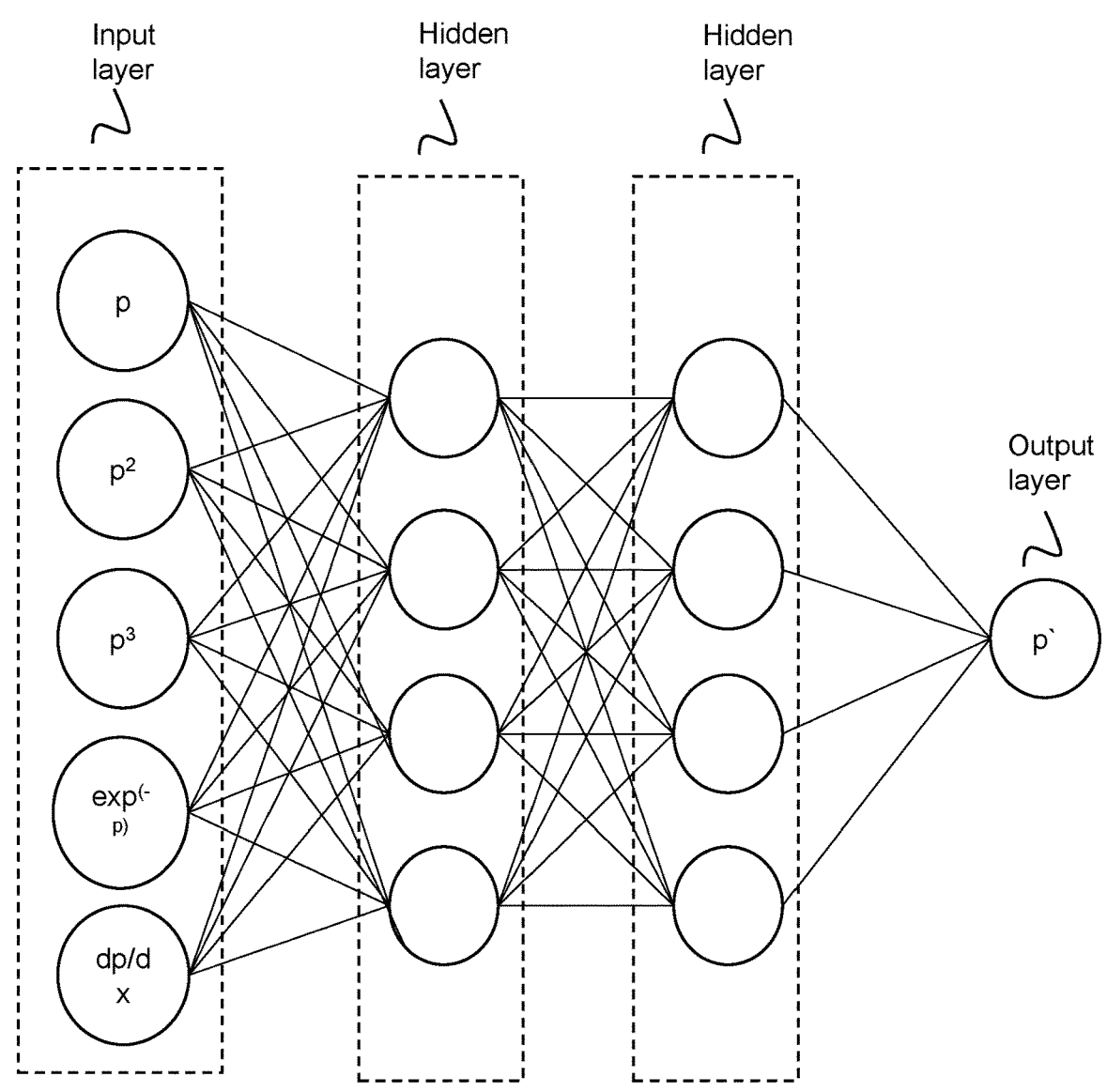
FIG. 5 is a schematic diagram illustrating an exemplary correction model according to some embodiments of the present disclosure.

FIG. 5 is a schematic diagram illustrating an exemplary correction model according to some embodiments of the present disclosure. As shown in FIG. 5, the correction model may include a DNN model. The correction model includes an input layer, two hidden layers, and an output layer. The input layer may include multiple nodes. Each of the multiple nodes may correspond to one type of input of the correction model. In some embodiments, each hidden layer may include 4 nodes. The output layer may include a node corresponding to the corrected projection data output by the correction model. Nodes of a network layer in the correction model may be connected to all nodes of a previous network layer. If the raw projection data is denoted as p, at least one term of the N-th power of a polynomial representation of the raw projection data employed herein may include two terms including $p^2$ and $p^3$, the first projection data is denoted as exp(–p), and the second projection data is denoted as dp/dx, the input layer includes 5 nodes corresponding p, p2, p3, exp(–p), and dp/dx. The raw projection data (e.g., p) and transformed projection data (e.g., p, p2, p3, exp(–p), and dp/dx), five types of input, may be input to the corresponding nodes in the input layer, and processed by the two hidden layers. The output layer may output the corrected projection data, denoted as p'.

The present disclosure also provides a system for correcting projection data. The system may include at least one storage device including a set of instructions or programs and at least one processor. The at least one processor may be configured to communicate with the at least one storage device. When executing the set of instructions or programs, the at least one processor is configured to cause the system to perform operations including obtaining raw projection data and transformed projection data determined based on the raw projection data, and obtaining corrected projection data by processing the raw projection data and the transformed projection data using a correction model. The raw projection data may be obtained by scanning an object using an imaging device. The transformed projection data may include at least one of: first projection data relating to radiation obstructed by the imaging device, or a portion thereof, second projection data relating to a position of the detector, or at least one of the N-th power of the raw projection data, wherein N is an integer greater than or equal to 2.

The present disclosure also provides a non-transitory computer-readable storage medium embodying a computer program product. The computer program product comprising instructions configured to cause a computing device to obtain raw projection data and transformed projection data determined based on the raw projection data and obtain corrected projection data by processing the raw projection data and the transformed projection data using a correction model. The raw projection data may be obtained by scanning an object using an imaging device. The transformed projection data may include at least one of: first projection data relating to radiation obstructed by the imaging device, or a portion thereof, second projection data relating to a position of the detector, or a portion thereof, or at least one of the N-th power of the raw projection data, wherein N is an integer greater than or equal to 2.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method, implemented on a computing device having one or more processors and one or more storage devices, comprising:
    obtaining raw projection data by scanning an object using an imaging device including a detector;
    determining, based on the raw projection data, transformed projection data, wherein the transformed projection data includes at least one of:
        first projection data relating to radiation obstructed by the imaging device, or a portion thereof, or
        second projection data relating to a position of the detector, or a portion thereof;
    obtaining corrected projection data by processing the raw projection data and the transformed projection data using a correction model, wherein the correction model includes a trained machine learning model; and
    generating a medical image of the object by reconstructing the corrected projection data.

2. The method of claim 1, further comprising:
    determining the first projection data based on exponential transformation of the raw projection data.

3. The method of claim 1, further comprising:
    determining the second projection data based on gradient information of the raw projection data, the gradient information relating to the position of the detector, or a portion thereof.

4. The method of claim 1, further comprising:
    obtaining the second projection data by performing a differential operation on the raw projection data based on the position of the detector, or a portion thereof.

5. The method of claim 1, wherein the imaging device includes a multi-energy computed tomography (CT) scanner, and the object is scanned by using the multi-energy CT scanner to emit a multi-energy ray for performing multi-energy imaging on the object.

6. The method of claim 1, wherein the correction model is obtained by a training process, the training process comprising:

obtaining a plurality of training samples each of which includes sample raw projection data, sample transformed projection data obtained based on the sample raw projection data, and standard projection data of a sample standard energy ray corresponding to the sample raw projection data; and determining the correction model by training a preliminary correction model using the plurality of training samples.

7. The method of claim 6, wherein the sample raw projection data of a training sample is obtained by a multi-energy imaging of a sample object, or a simulation thereof.

8. The method of claim 6, wherein the standard energy ray is a single energy ray.

9. The method of claim 6, wherein the standard projection data is obtained by polynomial fitting of the sample raw projection data.

10. The method of claim 1, wherein the corrected projection data is obtained by processing the raw projection data and the transformed projection data based on a correction coefficient group.

11. The method of claim 10, wherein the corrected projection data is obtained by performing polynomial fitting on the raw projection data and the transformed projection data based on the correction coefficient group.

12. The method of claim 10, wherein the correction coefficient group is determined based on one or more parameters determined from a correction model.

13. The method of claim 12, wherein the correction coefficient group includes a weight corresponding to each input of the correction model.

14. The method of claim 1, wherein the obtaining corrected projection data by processing the raw projection data and the transformed projection data comprises:

obtaining the corrected projection data by inputting the raw projection data and the transformed projection data into a correction model, wherein the correction model is a trained machine learning model.

15. The method of claim 1, wherein the transformed projection data further includes at least one term of an N-th power of a polynomial representation of the raw projection data, wherein N is an integer greater than or equal to 2.

16. A system for correcting projection data, comprising:

at least one storage device including a set of instructions or programs; and at least one processor configured to communicate with the at least one storage device, wherein when executing the set of instructions or programs, the at least one processor is configured to cause the system to perform operations including:

obtaining raw projection data by scanning an object using an imaging device including a detector;

determining, based on the raw projection data, transformed projection data, wherein the transformed projection data includes at least one of:

first projection data relating to radiation obstructed by the imaging device, or a portion thereof, second projection data relating to a position of the detector, or a portion thereof, or at least one term of an N-th power of a polynomial representation of the raw projection data, wherein N is an integer greater than or equal to 2;

obtaining corrected projection data by processing the raw projection data and the transformed projection data; and generating a medical image of the object by reconstructing the corrected projection data.

17. The system of claim 16, wherein the operations further include:

determining the first projection data based on exponential transformation of the raw projection data.

18. The system of claim 16, wherein the operations further include:

determining the second projection data based on gradient information of the raw projection data, the gradient information relating to the position of the detector, or a portion thereof.

19. The system of claim 16, wherein the imaging device includes a multi-energy computed tomography (CT) scanner, and the object is scanned by using the multi-energy CT scanner to emit a multi-energy ray for performing multi-energy imaging on the object.

20. A non-transitory computer-readable storage medium embodying a computer program product, the computer program product comprising instructions configured to cause a computing device to:

obtaining raw projection data-by scanning an object using an imaging device including a detector;

determining, based on the raw projection data, transformed projection data, wherein the transformed projection data includes at least one of:

first projection data relating to radiation obstructed by the imaging device, or a portion thereof, or second projection data relating to a position of the detector, or a portion thereof;

obtaining corrected projection data by processing the raw projection data and the transformed projection data using a correction model, wherein the correction model includes a trained machine learning model; and generating a medical image of the object by reconstructing the corrected projection data.

\* \* \* \* \*